US006177424B1

(12) United States Patent
Heindel et al.

(10) Patent No.: US 6,177,424 B1
(45) Date of Patent: Jan. 23, 2001

(54) 4'-SUBSTITUTED-4',5'-DIHYDROPSORALENS AND THERAPEUTICAL USES THEREOF

(76) Inventors: Ned D. Heindel, 200 Hexenkopf Rd., Easton, PA (US) 08042-9570; Jeffrey D. Laskin, 69 Lakeside Dr. North, Piscataway, NJ (US) 08854; Marilyn S. Whittemore, 2026 Widgeon Way Dr., Germantown, TN (US) 38138; Thomas E. McNeel, 3509 Amesbury, Memphis, TN (US) 38135; Christophe Guillon, Seeley G. Mudd Bldg., 6 E. Packer Hall, Bethlehem, PA (US) 18015; Diane E. Heck, 10 First St., Rumson, NJ (US) 07760; Robert D. Rapp, 1804 Elizabeth Ave., Laurel Dale, PA (US) 19605

(*) Notice: Under 35 U.S.C. 154(b), the term of this patent shall be extended for 0 days.

(21) Appl. No.: 09/450,560

(22) Filed: Nov. 30, 1999

Related U.S. Application Data
(60) Provisional application No. 60/110,336, filed on Nov. 30, 1998.

(51) Int. Cl.[7] .................. A61K 31/37; A61K 31/4433; C07D 493/04; C07D 405/14

(52) U.S. Cl. .............. 514/232.8; 514/314; 514/338; 514/455; 544/150; 546/152; 546/283.1; 549/282

(58) Field of Search ............ 549/282; 546/152, 546/283.1; 544/150; 514/232.8, 314, 338, 455

(56) References Cited

U.S. PATENT DOCUMENTS

| | | | |
|---|---|---|---|
| 4,124,598 | 11/1978 | Hearst et al. | 549/282 |
| 4,130,568 | 12/1978 | Confalone et al. | 546/283.1 |
| 4,196,281 | 4/1980 | Hearst et al. | 536/28 |
| 4,294,822 | 10/1981 | Kaufman | 424/59 |
| 4,950,770 | 8/1990 | Heindel et al. | 549/282 |
| 5,216,176 | 6/1993 | Heindel et al. | 549/280 |
| 5,356,929 | 10/1994 | Heindel et al. | 514/455 |
| 5,473,083 | 12/1995 | Heindel et al. | 549/280 |
| 5,625,079 | 4/1997 | Wollowitz et al. | 549/282 |
| 5,654,443 | 8/1997 | Wollowitz et al. | 549/282 |

FOREIGN PATENT DOCUMENTS

| | | |
|---|---|---|
| 95/00141 | 1/1995 | (WO). |

OTHER PUBLICATIONS

Wulff, Heike et al., " Alkoxypsoralens, Novel Nonpeptide Blockers of Shaker–Type K+ Channels: Synthesis and Photoreactivity", *Journal of Medicinal Chemistry*, 41, No. 23 pp. 4542–4549 (1988).

Beilstein Reg. No. 245419, not provided.

Adams, R. et al., "The Structure of the Compounds Produced from Olefins and Mercury Salts: Mercurated Dihydrobenzofurans", *The Journal of the American Chemical Society*, 1922, pp. 1781–1792.

Adams, R. et al., *Organic Reactions*, 1949, vol. 5., pp. 200–207.

Beckwith, Athelstan L.J. et al., Iododediazoniation of Arenediazonium Salts Accompanied by Aryl Radical Ring Closure, *The Journal of Organic Chemicals*, 1987, vol. 52, pp. 1922–1930.

Bravo, P. et al., "Total Synthesis of Homochiral 3–Deoxy–3–Fluoromuscarines", *Gazzetta Chimica Italiana*, 1990, pp. 275–276.

Cole, R.S., "Repair of DNA Containing Interstrand Crosslinks in *Escherichia coli*: Sequential Excision and Recombination", *Proc. Nat. Acad. Sci.*, 1973, pp. 1064–1068.

Corey, E.J. et al., "Total Synthesis of Picrotoxinin", *Journal of the American Chemical Society*, 1979, pp. 5841–5843.

Hearst, J., "Photochemistry of the Psoralens", *Chemical Research in Toxicology*, 1989, pp. 69–75.

(List continued on next page.)

Primary Examiner—Fiona T. Powers
(74) Attorney, Agent, or Firm—Morgan, Lewis & Bockius LLP

(57) ABSTRACT

The invention relates to 4'-substituted-4',5'-dihydropsoralen compounds of formula(V):

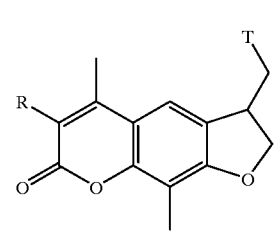

In the formula R is hydrogen, a halogen, CN or an acyl group; T is a halogen, CN, a carboalkoxy group $NR^1R^2$, or $(N^+R^1R^2R^3)X^-$, $R^1$ and $R^2$ are independently a $C_1-C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or heterocyclic aromatic ring; $R^3$ is hydrogen, a $C_1-C_{12}$ alkyl, or, when $R^1$ and $R^2$ together with the nitrogen form a heterocyclic aromatic ring, $R^3$ is a double bond within the heterocyclic aromatic ring; $X^-$ is a halide. In another embodiment, the invention relates to processes for preparing 4'-substituted-4',5'-dihydropsoralen compounds described above. The compounds of the invention have beneficial pharmaceutical properties and can be used alone or in pharmaceutical compositions used to treat a proliferative skin disorder and to treat microbial infections in a mammal by administering to the mammal an effective amount of a compound of the invention and then irradiating the mammal with ultraviolet light.

24 Claims, No Drawings

OTHER PUBLICATIONS

Heindel, N.D. et al., "Syntheses of Psoralen Analogues and Evaluation of Their Inhibition of Epidermal Growth Factor Binding", *Journal of Pharmaceutical Sciences,* 1991, pp. 686–689.

Isaacs, S.T. et al., "Synthesis and Characterization of New Psoralen Derivatives with Superior Photoreactivity with DNA and RNA", *Biochemistry,* 1977, pp. 1058–1064.

Kaufman, K.D. et al, "Synthetic Furocoumarins. I. A New Synthesis of Methyl–substituted Psoralenes and Isopsoralenes", *The Journal of Organic Chemistry,* 1961, pp. 117–121.

Kitano, K. et al., "Macrophage–Active Colony–Stimulating Factors Enhance Human Immunodeficiency Virus Type 1 Infection in Bone Marrow Stem Cells", *Blood : Journal American Society of Hematology,* 1991, pp. 1699–1705.

Laskin, J.D. et al., "A–Possible Mechanism of Psoralen Phototoxicity not involving Direct Interaction with DNA", *Proc. Natl. Acad. Sci.,* 1985, pp. 6158–6162.

Laskin, J.D. et al., "Basis for Natural Variation in Sensitivity to 5–Fluorouracil in Mouse and Human Cells in Culture", *Cancer Research,* 1979, pp. 383–390.

Laskin, J.D. et al., "Psoralen Binding and Inhibition of Epidermal Growth Factor Binding by Psoralen/Ultraviolet Light (PUVA) in Human Epithelial Cells", *Biochemical Pharmacology,* 1991, pp. 125–132.

Laskin, J.D. et al., Selective Inactivation of Lymphocytes after Psoralen/Ultraviolet Light (PUVA) Treatment Without Affecting Systemic Immune Responses, *Journal of Leukocyte Biology,* 1993, pp. 138–144.

Meijs, G.F. et al., Formation of Functionalized Dihydrobenzofurans by Radical Cyclization, *The Journal of American Chemical Society,* 1986, vol. 108, pp. 5890–5893.

Mills, L. et al, "Mercurated 1–Methyl–1,2–Dihydro–Benzofurans", *The Journal of American Chemical Society,* 1923, pp. 1842–1854.

Morison, W.L. et al., "Consensus Workshop on the Toxic Effects of Long–Term PUVA Therapy", *Archives of Dermatology,* 1998, pp. 595–598.

Orito, K. et al., "Synthesis of 5–Iodobenzofurans and 6–Iodobenzopyrans via Direct Iodination with Mercury(II) Oxide–Iodine Reagent", *Synthesis,* 1997, pp. 23–25.

Rai, S. et al., "Dramatic Improvements in Viral Inactivation with Brominated Psoralens, Naphthalenes and Anthracenes", *Photochemistry and Photobiology,* 1993, pp. 59–65.

Reitz, A.B. et al., "Stereoselectivity of Electrophile–Promoted Cyclizations of γ–Hydroxyalkenes. An Investigation of Carbohydrate–Derived and Model Substrates", *J. Org. Chem.,* 1987, pp. 4191–4202.

Stern, R. et al., "Cutaneous Squamous–Cell Carcinoma in Patients Treated with PUVA", *The New England Journal of Medicine,* 1984, pp. 1156–1161.

Yurkow, E.J. et al., "Mechanism of Action of Psoralens: Isobologram Analysis Reveals that Ultraviolet Light Potentiation of Psoralen Action is not Additive But Synergistic", *Cancer Chemother Pharmacology,* 1991, pp. 315–319.

4'-SUBSTITUTED-4',5'-DIHYDROPSORALENS AND THERAPEUTICAL USES THEREOF

This application claims priority to U.S. Provisional Application Ser. No. 60/110,336, filed Nov. 30, 1998, the disclosure of which is hereby incorporated by reference.

FEDERAL SUPPORT

This invention arose, at least in part, from research funded by NIH grants ES03647 and ES06897.

FIELD OF THE INVENTION

This invention relates to 4'-substituted-4,8-dimethyl-4',5'-dihydropsoralens and their use as phototherapeutics. Methods for preparing the 4'-substituted-4,8-dimethyl-4',5'-dihydropsoralens via ring closure reactions and synthetic intermediates are also described.

BACKGROUND OF THE INVENTION

Linear furocoumarins, also known as psoralens, have been used in combination with ultraviolet light for centuries in cosmetics and for the treatment of proliferative skin diseases such as, for example, vitiligo, eczema, mycosis fungoides, and psoriasis. Terms such as photosensitization, photochemotherapy, photopheresis and PUVA (psoralens ultra violet A radiation) are commonly used to refer to such methods. Recently it was discovered that by modifying the administration of psoralen and ultraviolet light to an offending condition, psoralens can be used to treat cancer (e.g., T cell lymphoma), autoimmune diseases, and microbial infection.

The basic structure of psoralen, with the ring numbering structure used throughout the specification, is shown below:

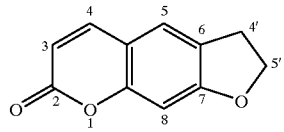

All psoralens contain two photo-activatable functions (absorbing in the UVA range)—an aryl-conjugated unsaturated pyrone (the coumarin portion) and an aryl-conjugated vinyl ether (the furan portion). All of the commercially available psoralens are highly lipophilic, non-nitrogenous, uncharged small molecules with minimal water solubility. Commercial psoralens are used in over-the-counter cosmetic creams, prescription pharmaceuticals, and as investigational candidates for many of the uses described above. The commercial psoralens in cosmetic/medical use include methoxsalen (also known as xanthotoxin, 8-methoxypsoralen or 8-MOP), trisoralen (also called 4,5', 8-trimethylpsoralen, TMP, or trioxsalen), and bergaptan (alternatively named 5-methoxypsoralen or 5-MOP).

The phototherapeutic action of psoralens has been discussed for example, by J. E. Hearst, "Photochemistry of the Psoralens," *Chemical Research in Toxicology*, 2, 69, (1989)) and T. F. Anderson and J. J. Vorhees, *Annual Reviews of Pharmacol. and Toxicol.*, vol. 10, p. 177, (1982). According to these articles, the highly lipophilic psoralens penetrate the target cell's membrane, intercalate into nuclear DNA, and photo crosslink the double helix through bis-cyclobutanes generated from the 3,4-double bond and the 4',5'-double bond [see numbering shown above] to double bonds in DNA's pyrimidine bases. Thus, because the crosslinked DNA is unable to uncoil and function as a template for new gene expression, the target cell is rendered non-viable.

A severe limitation to the acceptance of psoralen-based photochemotherapy or cosmetic skin pigment enhancement, however, is the risk of genetic mutations induced by DNA damage since the natural cellular level repair processes of bi-functional DNA-crosslinks are highly error-prone. Errors in cellular repair processes of true crosslinks translate to mutagenic/carcinogenic events and, in the clinical use of psoralens, represent a significant post-treatment risk of cancer. See, for example, R. S. Stern et al, "Cutaneous Squamous-cell Carcinoma in patients treated with PUVA," *New England J. of Med.*, pp. 1156–116 (1984); R. S. Stern et al, "Malignant Melanoma in Patients Treated for Psoriasis with Methoxsalen and Ultraviolet A Radiation (PUVA)," *New England J. of Med.*, vol. 336, pp 1041–1045 (1997); and W. L. Morrison et al. "Consensus Workshop of the Toxic Effects of Long-Term PUVA Therapy," *Arch. Dermatol.*, vol. 134, pp. 595–598 (1998).

The use of nonlinear furocoumarins (known as angelicins) for the treatment of psoriasis and other skin diseases is taught, for example by U.S. Pat. No. 4,312,883. According to the patent, nonlinear furocoumarins are effective photochemotherapeutic compounds that do not have the risks associated with psoralens. Nonlinear furocoumarins, however, are limited by their structural geometry, forming only non-crosslinked monoadducts which have diminished mutagenic behavior. See, for example, R. S. Cole, "Repair of DNA Containing Interstrand Crosslinks in *E. Coli*," *Proc. Nat. Acad. Sci.*, volume 70, p. 1064 (1973). Further, lipophilic linear psoralens, capable of forming only monoadducts, can be phototoxic to malignant cells. See J. VanDongen, N. D. Heindel et al., "Synthesis of Psoralen Analogs and Evaluation of their Inhibition of Epidermal Growth Factor Binding," *J. Pharm. Sci.*, volume 80, No. 7, pp. 686–689 (July 1991).

Despite such risks, an alternative mechanism exists, not involving DNA, by which psoralens can act as phototoxins to a cell. A 22 kDa receptor protein present on psoralen-sensitive cells has been identified as a binding site for photo-activated psoralens. Binding a psoralen to this nonnuclear receptor followed by UVA light activation of the psoralen blocks subsequent binding of epidermal growth factor (EGF) to that receptor. The existence of this nonnuclear target has been described in J. D. Laskin et al., "A Possible Mechanism of Psoralen Phototoxicity Not Involving Direct Interaction with DNA," *Proc. Nat. Acad. Sci.*, vol. 82, pp. 6158–6161, (September 1985).

U.S. Pat. Nos. 5,473,083 and 5,216,176 report that reduced and quaternized psoralens are valuable photoactivated therapeutics. Although promising as therapeutics, the 5'-substituted dihydro quaternary compounds have often been extremely difficult to synthesize. See, for example, copending U.S. patent application Ser. No. 09/199,552, filed Nov. 25, 1998, the disclosure of which is hereby incorporated by reference. Furthermore, no previous method existed for synthesis of 4'-(N-pyridiniummethyl)-4',5'-dihydropsoralen.

SUMMARY OF THE INTENTION

The invention provides a 4'-substituted-4,8-dimethyl-4',5'-dihydropsoralen of formula (V):

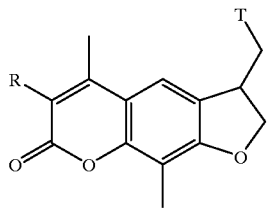

wherein
R is hydrogen, a halogen, CN, or an acyl group;
T is a halogen, CN, $NR^1R^2$, $(N^+R^1R^2R^3)X^-$, a carboxylate, or a carboalkoxy group,
$R^1$ and $R^2$ are independently a $C_1$–$C_6$ alkyl, or $R^1$ and $R^2$ together with the nitrogen form a 5–8 member heterocyclic ring, or when T is $(N^+R^1R^1R^3)X^-$, $R^1$ and $R^2$ together with the nitrogen form a 5–8 member heterocyclic ring or heterocyclic aromatic ring,
$R^3$ is hydrogen, a $C_1$–$C_{12}$ alkyl, or, when $R^1$ and $R^2$ together with the nitrogen form a heterocyclic aromatic ring, $R^1$ is a double bond within the heterocyclic aromatic ring;
$X^-$ is a halide.

The invention also relates to a process for preparing a 4'-substituted-4,8-dimethyl-4',5'-dihydropsoralen of formula (V) above where T is a halogen or CN. The process comprises the step of reacting a 4,8-dimethyl-6-diazoniumtetrafluoroborate-7-allyloxycoumarin of the formula (IV):

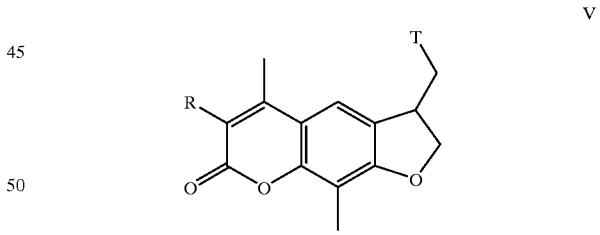

with a cyclization reagent under conditions to form a 4'-substituted-4,8-dimethyl-4',5'-dihydropsoralen. When T is Br, the cyclization reagent employed is $CuBr_2$. When T is I, the cyclization reagent is NaI with $I_2$. When T is cyano the cyclization reagent is CuCN.

Tertiary amino and quaternary ammonium derivatives of the 4'-substituted-4,8-dimethyl-4',5'-dihydropsoralens of the invention may be prepared from 4'-substituted-4,8-dimethyl-4',5'-dihydropsoralen of formula (V) where T is a halogen by displacing the halogen with an appropriate secondary or tertiary amine. Accordingly, in another embodiment, the invention relates to a method for preparing 4'-N-aminomethyl substituted 4,8-dimethyl-4',5'-dihydropsoralen of the formula (V):

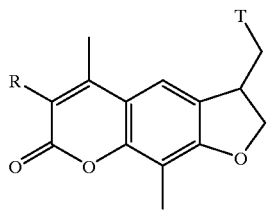

where

R is as defined above;
T is $NR^1R^2$ or $(N^+R^1R^2R^3)X^-$; and
$R^1$ and $R^2$ are independently a $C_1$–$C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or a 6-member heterocyclic aromatic ring;
$R^3$ is hydrogen, a $C_1$–$C_{12}$ alkyl, or, when $R^1$ and $R^2$ together with the nitrogen form a heterocyclic aromatic ring, $R^3$ is a double bond within the heterocyclic aromatic ring; and
X is bromide or iodide.

The method comprises reacting a compound of formula (V) where T is Br or I with a secondary amine of the formula $HNR^1R^2$ or $N^+R^1R^2R^3$ where $R^1$, $R^2$, and $R^3$ are as defined above.

The compounds of the invention have beneficial pharmaceutical properties and can be used alone or in pharmaceutical compositions used to treat a proliferative skin disorder and to treat microbial infections in a mammal by administering to the mammal an effective amount of a compound of the invention and then irradiating the mammal with ultraviolet light. Further, because of their inability to form crosslinks in the DNA, the compounds of the invention minimize the mutagenic/carcinogenic side effects long associated with psoralen-derived therapies.

Similarly, compounds of the invention and pharmaceutical compositions containing them may be used to treat a disease of the blood or bone marrow or to treat microbial infections in a mammal. Such a method comprising the steps of: obtaining cells from the blood or marrow of the mammal, introducing in vitro into the cells an effective amount of a compound according to the invention, exposing the cells containing the compound to ultraviolet radiation, and returning the cells to the blood or bone marrow of the mammal.

The compounds of the invention also have antimicrobial properties and can be used to control the growth of microorganisms on substrates and in aqueous systems.

DETAILED DESCRIPTION

1. Compounds of the Invention

This invention relates to 4'-substituted-4,8-dimethyl-4',5'-dihydropsoralens of the formula (V):

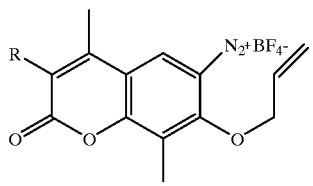

In formula (V), R is hydrogen, a halogen, CN or acyl. In a preferred embodiment, R is H, F, Br, I, propionyl, acetyl, or phenylacetyl; T is a halogen, CN, a carboxylate, a carboalkoxy group, or an amine of the formula $NR^1R^2$ or $(N^+R^1R^2R^3)X^-$. When T is a halogen, F, Br and I are preferred. When T is a carboalkoxy group, esters with 1 to 18 carbon atoms are preferred.

When T is an amine of the formula $NR^1R^2$, $R^1$ and $R^2$ are independently a $C_1$–$C_6$ alkyl, or $R^1$ and $R^2$ together with the nitrogen form a 5–8 member heterocyclic ring. An alkyl, according to the invention, may be straight chain or branched, substituted or unsubstituted with common substituents such as hydroxyl, halo, sulfonyl, amino, etc. The heterocyclic ring may likewise be substituted or unsubstituted. Preferably, $R^1$ and $R^2$ are independently methyl, ethyl, hydroxyethyl, or propyl, or $R^1$ and $R^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-($C_1$–$C_4$ alkyl)pyridinyl, N-hexamethyleneiminyl, or N-heptamethyleneiminyl. Most preferably, $R^1$ and $R^2$ are independently methyl, 2-hydroxyethyl, or propyl, or $R^1$ and $R^2$ together with the nitrogen form a heterocyclic ring selected from N-morpholinyl, N-pyridinyl, N-4-ethylpyridinyl, or N-4-methylpyridinyl.

In dihydropsoralens of formula (V) when T is $(N^+R^1R^2R^3)X^-$ the liphophilicity of the 4,8-dimethyl-4',5'-dihydropsoralen of the invention is increased. In formula (V) when T is $(N^+R^1R^2R^3)X^-$, $R^1$ and $R^2$ together with the nitrogen form a 5–8 member heterocyclic ring or heterocyclic aromatic ring, as just discussed mid $R^1$ and $R^2$ have the sane preferred embodiments as when T is $NR^1R^2$. $R^3$ is hydrogen, a $C_1$–$C_{12}$ alkyl, or, when $R^1$ and $R^2$ together with the nitrogen form a heterocyclic aromatic ring, $R^3$ is a double bond within the aromatic ring and $X^-$ is a halide. Preferably, $R^3$ is hydrogen, methyl, or ethyl, and X is a bromide or iodide.

Examples of dihydropsoralen compounds of formula V are:

4,8-Dimethyl-4'-(bromomethyl)-4',5'-dihydropsoralen;
4,8-Dimethyl-4'-(iodomethyl)-4',5'-dihydropsoralen;
4,8-Dimethyl-4'-(N-pyridiniummethyl)-4',5'-dihydropsoralen bromide salt;
4,8-Dimethyl-4'-(N-4-ethylpyridiniummethyl)-4',5'-dihydropsoralen bromide salt;
4,8-Dimethyl-4'-(N-4-methylpyridiniummethyl)-4',5'-dihydropsoralen bromide salt;
4,8-Dimethyl-4'-(N-quinoliniummethyl)-4',5'-dihydropsoralen bromide salt;
4,8-Dimethyl-4'-(N,N,N-trimethylammonium methyl)-4',5'-dihydropsoralen bromide salt;
3-Bromo-4,8-dimethyl-4'-(bromomethyl)-4',5'-dihydropsoralen;
3-Bromo-4,8-dimethyl-4'-(iodomethyl)-4',5'-dihydropsoralen;
3-Bromo-4,8-dimethyl-4'-(N-pyridiniummethyl)-4',5'-dihydropsoralen iodide salt;
3-Bromo-4,8-dimethyl-4'-(N-4-ethylpyridiniummethyl)-4',5-dihydropsoralen iodide salt;
3-Bromo-4,8-dimethyl-4'-(N-4-methylpyridiniummethyl)-4',5-dihydropsoralen iodide salt;
3-Bromo-4,8-dimethyl-4'-(N-quinoliniummethyl)-4',5'-dihydropsoralen bromide salt;
3-Bromo-4,8-dimethyl-4'-(N,N,N-trimethylammoniummethyl)-4',5'-dihydropsoralen bromide salt;
3-Bromo-4,8-dimethyl-4'-(N,N,N-trimethylammoniummethyl)-4',5'-dihydropsoralen iodide salt;
3-Iodo-4,8-dimethyl-4'-(iodomethyl)-4',5'-dihydropsoralen;
3-Cyano-4,8-dimethyl-4'-(bromomethyl)-4',5'-dihydropsoralen;
3-Cyano-4,8-dimethyl-4'-(iodomethyl)-4',5'-dihydropsoralen;
3-Cyano-4,8-dimethyl-4'-(N-pyridiniummethyl)-4',5'-dihydropsoralen bromide salt;
3-Cyano-4,8-dimethyl-4'-(N-pyridiniummethyl)-4',5'-dihydropsoralen iodide salt;
3-Cyano-4,8-dimethyl-4'-(N-4-ethylpyridiniummethyl)-4',5'-dihydropsoralen bromide salt;
3-Cyano-4,8-dimethyl-4'-(N-4-methylpyridiniummethyl)-4',5'-dihydropsoralen bromide salt;
3-Cyano-4,8-dimethyl-4'-(N,N,N-trimethylammoniummethyl)-4',5'-dihydropsoralen bromide salt;
3-Cyano-4,8-dimethyl-4'-(N,N,N-trimethylammoniummethyl)-4',5'-dihydropsoralen iodide salt;
3-Fluoro-4,8-dimethyl-4'-(bromomethyl)-4',5'-dihydropsoralen;
3-Fluoro-4,8-dimethyl-4'-(iodomethyl)-4',5'-dihydropsoralen;
3-Fluoro-4,8-dimethyl-4'-(N-pyridiniummethyl)-4',5'-dihydropsoralen bromide salt;
3-Fluoro-4,8-dimethyl-4'-(N-4-methylpyridiniummethyl)-4',5'-dihydropsoralen bromide salt;
3-Fluoro-4,8-dimethyl-4'-(N-4-methylpyridiniummethyl)-4',5'-dihydropsoralen bromide salt;
3-Fluoro-4,8-dimethyl-4'-(N-quinoliniummethyl)-4',5'-dihydropsoralen bromide salt;
3-Fluoro-4,8-dimethyl-4'-(N,N,N-trimethylammonium methyl)-4',5'-dihydropsoralen bromide salt;
3-Fluoro-4,8-dimethyl-4'-(iodomethyl)-4',5'-dihydropsoralen;
4,8-Dimethyl-4'-(N,N-diethanolaminomethyl)-4',5'-dihydropsoralen;
4,8-Dimethyl-4'-(N,N-dimethylaminomethyl)-4',5'-dihydropsoralen hydroiodide salt;
4,8-Dimethyl-4'-(N-morpholinomethyl)-4',5'-dihydropsoralen; and
4,8-Dimethyl-4'-(N-2,6-dimethylmorpholinomethyl)-4',5'-dihydropsoralen.

The photochemotherapeutic and/or chemotherapeutic compounds of the invention also include physiologically acceptable salts of the compounds of Formula V. Preferred physiologically acceptable salts are acid-addition salts. Common acceptable acid-addition salts include but are not limited to hydroiodic and hydrochloric acid salts, oxalate salts and tartrate salts.

2. Preparation of Compounds of the Invention

The compounds of the invention may be prepared according to general synthetic procedures. The examples below demonstrate the general synthetic procedures, as well as the specific preparation, of 4'-substituted-4',5'-dihydropsoralen compounds according to this invention. The examples are illustrative, and are not intended to limit in any manner, the claimed invention. While all the processes and synthetic procedures have been described using 4,8-dimethyl-substituted coumarins, considerable structural variation is, in fact, possible. The classic Pechmann synthesis (R. Elderfield, "Heterocyclic Compounds", II, Wiley & Sons, NY, p. 181 and 251(1951) and the versatile Kostanecki reaction (C. Hauser et al., "Organic Reactions", Vol. 8, p. 91 (1954) are capable of generating a wider variety of different 7-hydroxycoumarins to be employed as starting materials. These 7-hydroxycoumarins may be nitrated and then O-allylated followed by reduction to the amine and formation of the diazonium intermediate and cyclization leading to the 4'-substituted-4',5'-dihydropsoralens.

The diazonium tetrafluoroborate intermediates used in the process of the invention are prepared according to general synthetic procedures as taught, for example, by G. Meijs et al., *J. Am. Chem.* 108, 5890 (1986); A. Beckwith et al., *J Org. Chem.*, 52, 1922 (1987); and A. Roe, *Organic Reactions*, Vol. 5, R. Adams, ed. John Wiley and Sons, New York, pp. 204–206 (1949) the disclosures of which are herein incorporated by reference.

Generally, the diazonium tetrafluoroborate intermediates are prepared by nitration of 7-hydroxycoumarin with nitric acid in sulfuric acid to give 6-nitro-4-8-dimethyl-7-hydroxycoumarin 1 (see Example 1 below) which is then o-allylated by treatment with allyl bromide and potassium carbonate in dimethylsulfoxide to produce 6-nitro-4,8-dimethyl-7-allyloxycoumarin 2 (see Example 2 below). The 6-nitro-4,8-dimethyl-7-allyloxycoumarin is then reduced by treatment with tin(II) chloride, tin, and concentrated hydrochloric acid in ethanol to give 6-amino-4,8-dimethyl-7-allyloxycoumarin 3 (see Example 3 below). Finally, 6-diazoniumtetrafluoroborate-4,8-dimethyl-7-allyloxycoumarin 4 is formed by treatment with sodium nitrite in tetrafluoroboric acid (see Example 4 below).

The 4,8-dimethyl-4'-halomethyl-4',5'-dihydropsoralens of the invention are prepared by cyclizing the 6-diazoniumtetrafluoroborate-4,8-dimethyl-7-allyloxycoumarin intermediate discussed above with a cyclization reagent under conditions to form a 4'-substituted-4,8-dimethyl-4',5'-dihydropsoralen. The cyclization reagent used in a process of the invention differs for different substituents T. For example, when T is Br, the cyclization reagent is $CuBr_2$. When T is I, the cyclization reagent is NaI with $I_2$. When T is cyano the cyclization reagent is CuCN. In the cyclization step of the process for making the 4'-substituted-4,8-dimethyl-4',5'-dihydropsoralens according to the invention the nucleophile transferred is derived from an added reagent such as sodium iodide, copper (II) chloride, copper (II) bromide, or copper (I) cyanide, allowing different products to be generated from a single diazonium tetrafluoroborate intermediate. Yields depend on the efficiency of the radical generation and cyclization. As shown by Example 5 below, 6-diazoniumtetrafluoroborate-4-8-dimethyl-7-alloxycoumarin 4 cyclized readily to generate 4,8-dimethyl-4'-iodomethyl-4',5'-dihydropsoralen 5 in 95% yield with sodium iodide in acetone or, as shown by Example 7, to generate 4,8-dimethyl-4'-bromomethyl-4',5'-dihydropsoralen 7 in 56% yield with copper (II) bromide in dimethyl sulfoxide. Further, in Example 15, 4,8-dimethyl-4'-cyanomethyl-4',5'-dihydropsoralen 15 was generated in 42% yield with copper (I) cyanide in dimethylsulfoxide and pyridine.

Preferred processes for preparing the 4,8-dimethyl-4'-halomethyl-4',5'-dihydropsoralens or 4'-cyanomethyl-4',5'-dihydropsoralens are shown in Scheme 1 and described in more detail below and in the examples.

Scheme 1

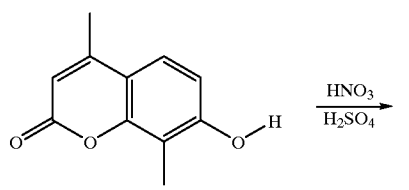

-continued

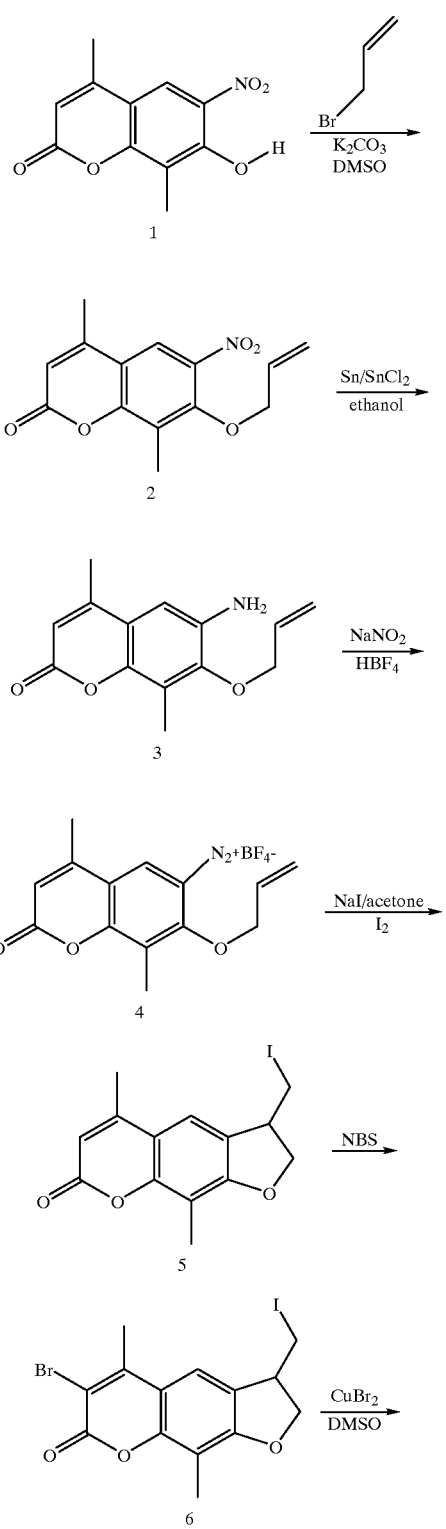

-continued

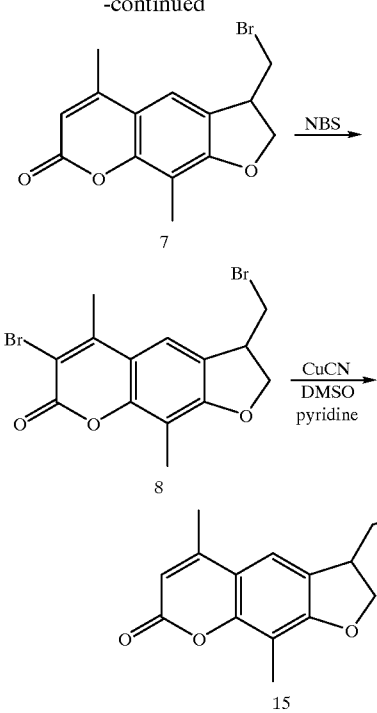

Tertiary amino and quaternary ammonium derivatives of the 4'-substituted-4,8-dimethyl-4',5'-dihydropsoralens of the invention may be prepared by displacing the bromine or iodine with an appropriate secondary or tertiary amine, such as pyridine, methyl pyridine, ethyl pyridine, morpholine, diethanolamine, and dimethylamine. As shown by Examples 9, 11, 12, 13 and 14, reacting the 4'-halomethyl-dihydropsoralens of Examples 5, 6, 7 or 8 with pyridine, the 4'-iodomethyl-dihydropsoralen 5 with pyridine gave 12–13% yield of the pyridinium iodide salt 9 and with 4"-methylpyridine gave 18% of the methylpyridinium iodide salt 11. The 3-bromo-4'-iodomethyl-4',5'-dihydropsoralen 6 gave 11% yield of the pyridinium iodide salt 12. A $^1$H-nmr study showed a transient exocyclic methylene intermediate with the generation of 4,8,4'-trimethylpsoralen as the major product (between 60–80%) when forming the pyridinium iodide salt 9 as shown in Example 9. Using refluxing morpholine, the corresponding morpholine derivative may be prepared. As shown by Examples 13 and 14, the 4,8-dimethyl-4'-bromomethyl-4',5'-dihydropsoralens showed a reduced tendency to dehydrohalogenate in the presence of pyridine with 4,8-dimethyl-4'-bromomethyl-4',5'-dihydropsoralen 7 yielding 43% of the pyridinium bromide salt 13 (Example 13) and 3-bromo-4,8-dimethyl-4'-bromomethyl-4',5'-dihydropsoralen 8 yielding 52% of the pyridinium bromide salt 14 (Example 14).

The 4,8-dimethyl-4'-halomethyl-4',5'-dihydropsoralens showed the same $C_3$ substitution that was evidenced with the 4,8-dimethyl-5'-halomethyl-4',5'-dihydropsoralens when treated with N-bromosuccinimide in chloroform or methylene chloride as described in copending U.S. patent application Ser. No. 09/199,552 filed Nov. 25, 1998, the disclosure of which is herein incorporated by reference. As shown by Examples 6 and 8,4,8-dimethyl-4'-iodomethyl-4',5'-dihydropsoralen 5 (of Example 5) gave 3-bromo-4,8-dimethyl-4'-iodomethyl-4',5'-dihydropsoralen 6 (Example 6) in 92% yield with N-bromosuccinimide and 4,8-dimethyl-4'-bromomethyl-4',5'-dihydropsoralen 7 (Example 7) gave 3-bromo-4,8-dimethyl-4'-bromomethyl-4',5'-dihydropsoralen 8 in 76% yield (Example 8).

In a preferred embodiment, quaternary ammonium derivatives of the 4'-substituted-4,8-dimethyl-4',5'-dihydropsoralens of the invention are prepared by reaction with 4'-halomethyl-dihydropsoralens as shown by Scheme 2 below and described in more detail in the examples. Scheme 2:

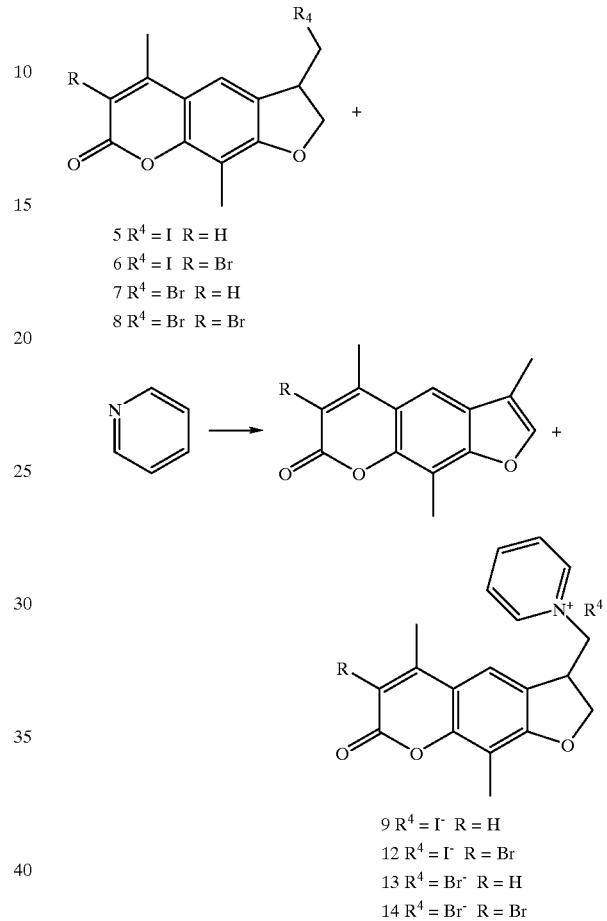

The bromide and iodide anions in the quaternary ammonium salts may be exchanged for other anions (e.g., chloride or another pharmaceutically acceptable anion) by ion exchange on a resin charged with the desired anion.

3. Pharmacological Activity

The 4'-substituted-4',5'-dihydropsoralens according to the invention are photochemotherapeutic compounds useful to prevent or treat skin, blood, marrow diseases, and microbial infections in a mammal. Treatment of a disease according to the invention encompasses not only treating an existing condition but treatment to prevent the disease condition from occurring. Examples of diseases treatable by compounds of the invention include cancer, infections, Acquired Immuno Deficiency Syndrome, HIV, cutaneous T-cell lymphoma, scleroderma, vitiligo, myasthenia gravis, multiple sclerosis, rheumatoid arthritis and other arthridides, psoriasis, inflammation, lupus erythematosus, tuberculosis, and the like.

Compounds of the invention have demonstrated photoinduced activity in an in vitro growth inhibition assay against PAM 212 keratinocytes. Psoriasis, mycosis fungolides, eczema, scleroderma, cancer, and similar proliferative diseases are often characterized by abnormal cell growth regulation. Application of PUVA therapy to correct proliferative disorders on the skin or internally, especially psoriasis, is one clinical expression of photochemotherapy. The use of the assay described in Example 16 is based on the observation that phototherapeutics are extremely potent inhibitors of growth factor binding in mammalian cells including humans and this inhibition arrests the proliferative disorder. This assay was performed in the cell culture laboratory. For a discussion of cell growth assays see, e.g:, J. Laskin et al., Cancer Research, vol. 39, pp. 383–390 (1979) and E. Yurkow and J. Laskin, Cancer Chemotherapy and Pharmacology, vol. 27, pp. 315–319, (1991). Inhibition of cell growth is dependent on dose ol the phototherapeutic and on the quanta of light in the 320–400 nm wavelength (ultraviolet light A). It is also structure-dependent, that is, there is a direct correlation between those specific phototherapeutics currently used that are clinically active and their ability to inhibit the growth of the cells.

Accordingly, one embodiment of the invention relates to a method of treatment of a skin disease in a mammal in recognized need thereof. The method comprises administering to the mammal an effective amount of a 4'-substituted-4',5'-dihydropsoralen and irradiating the mammal with sufficient UVA light to effect photochemical sensitization on the skin. The 4'-substituted-4',5'-dihydropsoralen may be administered topically or systemically. Generally, the dosage of UV applied is that conventionally used in the photochemical treatment of skin and preferably ranges from about 0.2 to about 15 joules/cm$^2$. The amount and duration of irradiation will depend upon a number of factors including the type and the extent of the disease being treated, the age of the patient, and will be apparent to one skilled in the art. The frequency of treatment will also depend upon such factors and will also be apparent to one skilled in the art.

The 4'-substituted-4',5'-dihydropsoralens of the invention may also be used to treat diseases of the blood or bone marrow in a patient. Accordingly, the invention also relates to a process for the treatment of diseases of the blood or bone marrow in a patient in need of such treatment. The process comprises obtaining cells from the blood or bone marrow of the patient, contacting the cells in vitro with a 4'-substituted-4',5'-dihydropsoralen according to the invention, exposing the cell in contact with the 4'-substituted-4',5'-dihydropsoralens with sufficient UVA to activate the therapeutic effect of the 4'-substituted- 4',5'-dihydropsoralens and returning the cells to the patient's blood stream or bone marrow.

In another embodiment, the patient is dosed in vivo with the psoralen and the cells of the blood or bone marrow subsequently removed, irradiated ex vivo, and subsequently returned to the patient.

Methods for treating blood cells and marrow are known in the art and taught, for example, by U.S. Pat. No. 5,356,929, the disclosure of which is herein incorporated by reference. Blood cells may be obtained from a patient using any ordinary conventional technique. Bone marrow may be obtained using established protocols available to those in the art and described, for example, in Kitano et al., Blood 77:1699–1705 (1991) or Folks et al., Science 242:919–922 (1988). White blood cells may be separated from pigmented cells (red blood cells) and other factors using the common technique of leukopheresis. If necessary, subpopulations of cells of interest from either the blood or bone marrow may be separated from the remainder of cells in the sample using a combination of techniques including centrifugation and flow cytometry. Cells so isolated are then either irradiated (in the case of the patient to whom the drug has already been administered), or they are treated with the compound of choice in a manner similar to that described above for the treatment of cells in culture followed by irradiation. Essentially, the phototherapeutic compound is dissolved in isotonic buffered solution and is added to the cells in a therapeutically effective amount to be determined by the extent and type of disease being treated, and the number of cells in the sample. After a period of incubation, treated cells are exposed to ultraviolet light (UVA, 320–400 nm) as described above. In some cases, depending on the compound involved, different wavelengths of light may also be used. After exposure to light, the cells are washed in an isotonic, buffered solution and are returned to either the patient's blood or bone marrow using conventional technology.

The compounds of the invention which are capable of intercalating into double-stranded nucleic acid, i.e., 4'-substituted-4',5'-dihydropsoralens, may also be used to eliminate or reduce the levels of infectious agents in blood. Blood may be treated with such a compound under the conditions described above and be subsequently irradiated with UVA. This treatment has advantages over known treatments which use psoralen compounds that also form crosslinks in double stranded nucleic acid. In the later case, residual psoralen remaining in the blood sample is potentially quite mutagenic to a patient receiving such blood, e.g., during a transfusion. In the former case, residual t'-substituted-4',5'-dihydropsoralen is potentially far less mutagenic to a recipient of the blood because of the inability of these compounds to form crosslinks in the DNA.

Accordingly, in another embodiment, the invention relates to a method for reducing the level of infectious agents in the blood or bone marrow of a mammal. The method comprises the steps of obtaining cells from the blood or bone marrow of a mammal, introducing into the cells an effective amount of a 4'-substituted-4'-5'-dihydropsoralen according to the invention, exposing the cell in contact with the 4'-substituted-4',5'-dihydropsoralens with sufficient UVA to activate the therapeutic effect of the 4'-substituted-4',5'-dihydropsoralens. Such methods are known in the art and described for example, in U.S. Pat. Nos. 5,789,150; 5,658, 722; 5,459,030 and 5,288,605, the disclosures of which are herein incorporated by reference.

The 4'-substituted-4',5'-dihydropsoralen derivatives according to the invention also have antimicrobial effects. Accordingly, the invention provides a method of treating microbiological infections in a mammal in recognized need thereof. The method comprises administering to the mammal an effective amount of a 4'-substituted-4',5'-dihydropsoralen derivative according to the invention. Examples of organisms that can be treated by a process according to the invention include A. Niger, Chlorella, Mycobacterium tuberculosis and fungal organisms, such as dermatophytes, Trichophyton, Microsporum and Epidermophyton, different Candida species, Trichoderma, Cryptococcus, Aspergillus Zygomyetes, Fusarim which can cause infections in humans and animals. Histoplasmosis, Blastomyces, and Coccidioides, for example, can cause lower respiratory infections. Trichophyton rubrum causes difficult to eradicate nail infections. Hendersonula toruloidea and Scopulariopsis brevicaulis are known to cause tinea pedis, tinea captitis, tinea cruris and different ring worm infections.

Due to their valuable pharmacological properties, the compounds of the invention or their physiologically acceptable salts, are particularly suitable for use as active compounds in pharmaceutical compositions. The 4'-substituted-4',5'-dihydropsoralens of the invention can be either administered alone or in mixtures with one another or with other therapeutic agents. As mentioned above, the 4'-substituted-4',5'-dihydropsoralens and of the invention may be applied topically in the form of an ointment or lotion, administered orally, intravenously, or parenterally. Methods for preparing clinically-really compositions are conventional in this art and include gelatin capsules or tablets for oral administration, solutions or ointments for external use, as described, for example, in U. S. Pat. No. 5,356,929. The compounds according to the invention can be administered orally, topically, rectally, anterally, internally, by boluses or, if desired, parenterally. Topical or oral administration may be preferred.

The invention also relates to photochemotherapeutic and chemotherapeutic pharmaceutical compositions for use in treating diseases such as those discussed above. A pharmaceutical composition according to the invention comprises a therapeutically effective amount of a 4'-substituted-4',5'-dihydropsoralen with or without a pharmaceutically acceptable carrier or agent. Preferably, a pharmaceutical composition according to the invention contains a 4'-substituted-4',5'-dihydropsoralen or in a therapeutically effective amount to treat a disease of the skin, blood or marrow of a mammal, in particular, a human. For treatment of microbial infections, such as tuberculosis, the pharmaceutical composition contains a 4'-substituted-4',5'-dihydropsoralen or in a therapeutically effective amount to treat the microbial infection. Pharmaceutically acceptable carriers are known in the art and are described, for example, in U.S. Pat. Nos. 4,124,598 and 4,130,568, the disclosures of which are herein incorporated by reference.

Pharmaceutical compositions of the invention may further include excipient, stabilizers, emulsifiers, therapeutic adjuvants, diluents and the like and may be provided in sustained release or timed release formulations. Suitable solid or liquid formulations are, for example, granules, powders, coated tablets, microcapsules, suppositories, syrups, elixirs, suspensions, emulsions, drops or injectable solutions. Commonly used additives in protracted release preparations are excipients, disintegrates, binders, coating agents, swelling agents, glidants, or lubricants, flavors, sweeteners or solubilizers. More specifically, frequently used additives are, for example, magnesium stearate, magnesium carbonate, titanium dioxide, lactose, mannitol and other sugars, talc, lactalbumin, gelatin, starch, cellulose and its derivatives, animal and vegetable oils, polyethylene glycols and solvents. Common solvents include sterile water and monohydric or polyhydric alcohols such as glycerol. Acceptable carriers, agents, excipient, stabilizers, diluents and the like for therapeutic use are well known in the pharmaceutical field, and are described, for example, in Remington's *Pharmaceutical Sciences*, Mack Publishing Co., ed. A. R. Gennaro (1985). If appropriate, the compound may be administered in the form of a physiologically acceptable salt, for example, an acid-addition salt.

The pharmaceutical compositions are preferably produced and administered in dosage units, each unit containing as an active component an effective dose of at least one compound of the present invention and/or at least one of its physiologically acceptable salts. In the case of mammals, the effective dose to treat diseases such as those discussed above can range from about 1 to about 100 mg/kg of body weight per day.

The pharmaceutical compositions according to the invention are suitable for use in effecting photochemical sensitivity on the skin of a mammal, particularly a human patient or subject, and comprise an effective amount of a 4'-substituted-4',5'-dihydropsoralen compound according to the invention and a pharmaceutically acceptable carrier or diluent. Such compositions are well known in the art and taught, for example, by U.S. Pat. Nos. 4,124,598 and 4,130,568, the disclosures of which are herein incorporated by reference.

For oral treatment, the active ingredient is generally formulated in tablets or in gelatin capsules. In such a case, the diluent may, if desired, may be used. For topical applications, solutions or ointments may be prepared and employed. These may be formulated with any one of a number of pharmaceutically acceptable carriers, as is well known in the art. Administration may be, for example, in the form of tablets, capsules, powders, syrups, or solutions, or as already stated in the form of ointments, creams, or solutions for topical use.

For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg to about 50 mg, preferably from about 5 to about 10 mg, per kg ol body weight. Such administration and selection of dosage and unit dosage will of course have to be determined according to established medical principles and under the supervision of the physician in charge of the therapy involved.

Topical formulations comprise an effective amount of the active ingredient per unit area. Preferably, the topical formulation is in the form of a one percent solution, suspension or ointment and is applied on the skin at about 0.1 mL per square centimeter. The formulations contain a suitable carrier, such as, ethanol or any of the pharmaceutically acceptable carriers described above. A typical formulation for a 1% phototherapeutic lotion comprises:

(A) 25 ml of propylene glycol;
(B) 1 ml of triethanolamine;
(C) 12 ml of water;
(D) 1.5 grams of oleic acid;
(E) 10.5 grams of polyethylene glycol 400 monostearate;
(F) 10 ml of silicon fluid DC-200;
(G) 10 ml of CARBOPOL 934, 2% mucilage; and
(H) 1 gram of at least one 4'-substituted-4',5'-dihydropsoralen according to the invention.

4. Microbicide Activity and Methods of Use

The 4'-substituted 4',5'-dihydropsoralens according to the invention are useful in preventing the microbiological attack, degradation, or deterioration of various types of raw materials and products such as leather, textiles, plastics, plastic containers, pulp, paper and paperboard, coatings, lumber, as well as agricultural products such as seeds and crops. Accordingly, additional embodiments of the invention employ the combination to control the growth of microorganisms on or in such industrial products, raw materials or processes.

Accordingly, another embodiment of the invention provides a microbicide composition. The composition contains a 4'-substituted-4',5'-dihydropsoralen in an amount effective to control the growth of at least one microorganism. The invention also provides a method for controlling the growth of a microorganism on a substrate. This method contacts a substrate susceptible to the growth of microorganisms with an effective amount of a 4'-substituted 4',5'-dihydropsoralen to control the growth of at least one microorganism on the substrate. The invention further provides a method for controlling the growth of microorganisms in an aqueous system capable of supporting growth of a microorganism. This method treats the aqueous system with an amount of a 4'-substituted 4',5'-dihydropsoralen effective to control the growth of at least one microorganism in the aqueous system.

Depending on the application, microbicide compositions according to the invention may be prepared in various forms known in the art. For example, the composition may be prepared in liquid form as an aqueous solution, dispersion, emulsion, or suspension, a dispersion or suspension in a non-solvent, or as a solution by dissolving a 4'-substituted 4',5'-dihydropsoralen in a solvent or combination of solvents. Suitable solvents include, but are not limited to, methyl ethers of glycols, M-pyrol or 1-methylpyrrolidinone, or petroleum distillates. The microbicide composition may be prepared as a concentrate for dilution prior to its intended use or in a liquid composition or system, such as an aqueous composition or system. Common additives such as surfactants, emulsifiers, dispersants, and the like may be used as known in the art to increase the solubility of the 4'-substituted-4',5'-dihydropsoralen.

Microbicide compositions of the invention may also be prepared in solid form, for example as a powder or tablet, using means known in the art. For example, a liquid product containing a 4'-substituted-4',5'-dihydropsoralen is deposited on carriers such as diatomaceous earth or kaolin. The resulting solid or solids may be mixed together or one solid may be mixed with the other component, or a solution or liquid formulation containing the component, to form a powder or tablet.

According to the invention, control of the growth of a microorganism on a substrate or in an aqueous system means control to, at, or below a desired level and for a desired period of time for the particular substrate or system. This can vary from complete prevention or inhibition of microbiological growth to controlling microbiological growth at a certain desired level and for a desired time. The 4'-substituted-4',5'-dihydropsoralens described here can, in many cases, reduce the total microbiological count to undetectable limits and maintain the count at that level for a significant period of time. Accordingly, the combination may be used to preserve a substrate or system.

The effective amount or percentage of a 4'-substituted-4',5'-dihydropsoralen necessary to achieve the desired result will vary somewhat depending on the substrate or aqueous system to be protected, the conditions for microbial growth, the particular microbicide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 1.0%. With aqueous systems, an effective amount may range from about 0.5 to about 10,000 parts per million, more preferably from about 5 to about 5000 parts per million of the aqueous system, and most preferably from, about 10 to about 1000 parts per million. Similar amounts effectively control slime formation. For slime control, effective amounts preferably range from about 1 to about 1000 parts per million, and more preferably, from about 1 to about 200 parts per million of the aqueous system.

A microbicide composition containing a 4'-substituted-4',5'-dihydropsoralen may be applied in a variety of industrial uses and processes for microorganism control. The 4'-substituted-4',5'-dihydropsoralens may be used in place of and in the same manner as other microbiocides traditionally used in the particular industry. As discussed above, such industries include, but are not limited to the leather industry, the lumber industry, the papermaking industry, the textile industry, the agricultural industry, and the coating industry. The 4'-substituted-4',5'-dihydropsoralens may also be used with aqueous systems such as those previously discussed which are subject to microbiological attack and degradation. The problems caused by microbiological attack and deterioration in these various applications has been described above.

EXAMPLES

The following examples demonstrate the preparation of compounds according to the invention. The examples are illustrative, and are not intended to limit, in any manner, the claimed invention.

Chemicals and solvents were obtained from commercial sources and used without further purification unless otherwise stated. Starting materials were purchased from Aldrich Chemical, unless otherwise specified. Melting points were determined on a Mettler FP 81 MBC cell with a Mettler FP 80 central processor. Elemental analyses were determined by Oneida Research Services, Wliiesboro, N.Y. Proton nmr spectra were recorded on a Bruker AC 250 operated at 250.13 MHz in the FT mode using deuterated solvents. Chemical shifts were reported in ppm ($\delta$) downfield from tetramethylsilane. Chemical shifts were reported in the following order: (multiplicity, number of protons, coupling constants in Hz). Multiplicity is designated as follows: s (singlet), d (doublet), t (triplet), q (quartet), and m (multiplet). The decoupled carbon nmr spectra were recorded on the Bruker AC 250 operating at 62.89 MHz in the FT mode. Deuterated solvents employed included deuteriochloroform, dimethyl sulfoxide-$d_6$, acetone-$d_6$ and methanol-$d_4$; these served as an internal reference for carbon spectra. Structural determination also included COSY, DEPT and HETCOR experiments. Gas chromatography/mass spectrometry was run on a Varian gas chromatograph 3300 model in series with a Finnegan ITS 40™ Magnum Ion Trap Mass Spectrometer. High performance liquid chromatography analyses were run on a Hewlett Packard HP 1050 Series model.

I. Synthesis of Precursors For the Diazonium Tetrafluoroborate Ring Closure

Example 1

6-Nitro-4,8-dimethyl-7-hydroxycoumarin 4,8-Dimethyl-7-hydroxycoumarin (7.50 g, 39.4 mmoles) was dissolved in 75 ml concentrated sulfuric acid at room temperature and chilled to −20° C. before the addition of chilled nitrating mixture (3 ml concentrated nitric acid added to 9 ml concentrated sulfuric acid). Stirring was continued for three hours at −20° C. with the mixture allowed to warm before pouring into ice. Bright yellow crystals were filtered, washed with water and dried to recover 7.50 g (81% yield). The product was recrystallized from ethanol to give yellow green crystals: mp 229.5–231.5° C.; $^1$H-nmr (dimethyl sulfoxide-$d_6$):$\delta$ 2.29 (s, 3H), 2.41 (s, 3H), 6.37 (s, 1H), 8.19 (s, 1H), 11.30 (s, 1H); $^{13}$C-nmr (dimethyl sulfoxide-$d_6$):$\delta$ 8.8, 18.0, 112.4, 112.9, 115.1, 119.9, 132.8, 152.9, 154.2, 155.1, 159.0; ms: (EI) m/z (relative intensity) 236 ($M^+$, 23), 235 ($M^+$, base) 207 (84), 77 (30).

Anal. Calcd. for $C_{11}H_9NO_5$: C, 56.18; H, 3.86; N, 5.96. Found: C, 55.94; H, 3.79; N, 5.96.

Example 2

6-Nitro-4,8-dimethyl-7-allyloxycoumarin

The 6-nitro-4,8-dimethyl-7-hydroxycoumarin (5.00 g, 21.2 mmoles) of Example 1 was mixed with dried $K_2CO_3$ (12.8 g, 93.0 mmoles) in 100 ml dimethyl sulfoxide and heated to reflux before the addition of allyl bromide (12.9 g, 106 mmoles) was carried out dropwise with stirring. Refluxing was continued overnight. Solids were removed by filtration and solvent evaporated to isolate the product. The crude product was placed under vacuum to remove residual dimethyl sulfoxide. The yield was 4.85 g (83% yield). Recrystallization from 2-propanol yielded bright yellow crystals: mp 158.3–158.8° C.; $^1$H-nmr (dimethyl sulfoxide-d$_6$):δ 2.31 (s, 3H), 2.41 (s, 3H), 4.54 (d, j=5.6 Hz, 2H), 5.25 (d, 1H), 5.38 (d, 1H), 5.98–6.10 (m, 1H), 6.48 (s, 1H), 8.20 (s, 1H); $^{13}$C-nmr (dimethyl sulfoxide-d$_6$):δ 9.4, 18.1,75.8, 114.4, 115.8, 119.1, 119.5, 122.0, 132.7, 140.6, 151.6, 152.7, 154.2, 158.9.

Anal. Calcd. for C$_{14}$H$_{13}$NO$_5$ 0.17 H$_2$O: C, 60.40; H, 4.83; N, 5.03. Found: C, 60.40; H, 4.74; N, 5.02.

Example 3

6-Amino-4,8-dimethyl-7-allyloxycoumarin

To a round bottom flask was added finely ground 6-nitro-4,8-dimethyl-7-allyloxycoumarin of Example 2 (3.00 g, 10.9 mmoles), tin (3.24 g, 27.3 mmoles), tin (II) chloride (3.04 g, 16.0 mmoles) and 9 ml concentrated hydrochloric acid in 200 ml ethanol. The mixture was stirred overnight during which all tin dissolved. Most of the ethanol was removed in vacuo. As the solution was allowed to cool, a gel formed which was filtered to recover a small amount of pearlized crystals (the hydrochloride salt). Water was added and a drop of iso-amyl alcohol was added to prevent frothing as solid sodium bicarbonate was added with stirring until the solution was basic. Ether was added to the filtrate arid a precipitate formed which was filtered and rinsed with ether to remove tin (II) chloride. The solids were dried and extracted with hot ethanol on the funnel of a filtration flask. Evaporation of the ethanol gave a crude product that was recrystallized from ethanol to provide 2.20 grams (82% yield) bright mustard yellow crystals: mp 145.6–147.4° C.; $^1$H-nmr (dimethyl sulfoxide-d$_6$):δ 2.28 (s, 3H), 2.49 (s, 3H), 4.54 (d, 2H), 5.28 (d, 1H), 5.48 (d, 1H), 5.98–6.32 (m, 1H), 6.39 (s, 1H), 7.58 (s, 1H); $^{13}$C-nmr (dimethyl sulfoxide-d$_6$):δ 9.4, 18.1, 74.6, 113.6, 115.1, 116.0, 118.7, 120.1, 125.5, 133.5, 147.0, 151.5, 152.5, 159.6.

Anal. Calcd. for C$_{14}$H$_{15}$NO$_3$: C, 68.56; H, 6.93; N, 5.66. Found: C, 68.34; H, 6.98; N, 5.52.

Example 4

6-Diazoniumtetrafluoroborate-4,8-dimethyl-7-allyloxycoumarin

The 6-amino-4,8-dimethyl-7-allyloxycoumarin (1.00 g, 4.08 mmoles) of Example 3 was added to 3.36 ml tetrafluoroboric acid (24% aqueous) and chilled in an ice/acetone bath before the addition of a 40% aqueous sodium nitrite solution (0.714 g) in 1 ml water. A precipitate formed instantly with much frothing. After fifteen minutes, the solids were collected by filtration, rinsed with a minimal amount of 5% cold tetrafluoroboric acid, ice cold methanol, and rinsed again with ether. The solids were used without further drying. The weight recovered was 0.685 g (82% yield). Recrystallization of solids from acetone/ether afforded tan crystals: mp 139–141° C.; $^1$H-nmr (CD$_2$OD):δ 2.50 (s, 6H), 5.02 (d, 2H), 5.48 (d, 1H), 5.61 (d, 1H), 6.14–6.35 (m, 1H), 6.57 (s, 1H), 8.91 (s, 1H).

Anal. Calcd. for C$_{11}$H$_{13}$BF$_4$N$_2$O$_3$: C, 48.87; H, 3.81; N, 8.14. Found: C, 48.68; H, 3.89; N, 7.94.

II. Synthesis of 4,8-dimethyl-4'-halomethyl-4',5'-dihydropsoralens

Example 5

4,8-Dimethyl-4'-iodomethyl-4',5'-dihydropsoralen

Sodium iodide (0.680 g, 4.50 mmoles) was added to 15 ml acetone with a small crystal of I$_1$ added. Separately, the 6-diazoniumtetrafluoroborate-4,8-dimethyl-7-allyloxycoumarin (0.775 g, 2.23 mmoles) of Example 4 was dissolved in acetone and added dropwise to the sodium iodide/I$_2$ solution. After fifteen minutes, the solvent was removed in vacuo. The solids were taken up in chloroform, washed with water and aqueous bisulfite and dried over magnesium sulfate. Evaporation of the solvent recovered crystals that weighing 0.750 g (95% crude yield). Recrystallization from ethanol yielded white crystals: mp 179–180° C.; $^1$H-nmr (deteriochloroform):δ 2.16 (s, 3H), 2.42 (s, 3H), 3.19 (t ,j=9.5 Hz, 1H), 3.35 (dd, J$_1$=10 Hz, J$_2$=5 Hz, 1H), 3.78–3.92 (m, 1H), 4.38 (dd, J$_2$=10 Hz, J=5 Hz, 1H), 4.65 (t, J=9.1 Hz, 1H), 6.10 (s, 1H), 7.20 (s, 1H); $^{13}$C-nmr (dimethyl sulfoxide-d$_6$):δ8.7, 11.8, 19.5, 44.7, 79.7, 108.1, 111.6, 114.8, 119.7, 126.9, 154.6, 154.8, 161.5, 163.1; ms: (EI) m/z (relative intensity) 357 (M$^+$, 22), 356 (M$^+$, 55) 230 (14), 229 (base), 187 (26).

Anal. Calcd. for C$_{14}$H$_{13}$IO$_3$: C, 47.21; H, 3.68. Found: C, 47.27; H, 3.64.

Example 6

3-Bromo-4,8-dimethyl-4'-iodomethyl-4',5'-dihydropsoralen

The 4,8-dimethyl-4'-iodomethyl-4',5'-dihydropsoralen (135 mg, 0.379 mmoles) of Example 5 was taken up in 15 ml methylene chloride, to which was added N-bromosuccinimide (68 mg, 0.382 mmoles) and reaction mixture was stirred overnight. The solvent was evaporated and the resulting solids were taken up in chloroform, washed with saturated aqueous bisulfite, two 1 ml portions of water, and then dried over magnesium sulfate before the solvent was evaporated. After recrystallization from ethanol, the weight recovered was 165 mg (92% yield) tan crystals: mp 205.7–205.9° C.; $^1$H-nmr (deuteriochloroform):δ 2.29 (s, 3H), 2.51 (s, 3H), 3.19 (t, J=9.5 Hz, 1H), 3.39 (dd, 1H), 3.75–3.87 (m, 1H), 4.40 (t, 1H), 4.67 (t, 1H), 7.16 (s, 1H); ms: (EI) m/z (relative intensity) 437 (M$^+$, 23), 436 (M$^+$, 86) 435 (base), 309 (15), 308 (49), 307 (19).

Anal. Calcd. for C$_{14}$H$_{12}$BrIO$_3$: C, 38.65; H, 2.78. Found: C, 38.66; H, 2.61.

Example 7

4,8-Dimethyl-4'-bromomethyl-4',5'-dihydropsoralen

6-Diazoniumtetrafluoroborate-4,8-dimethyl-7-allyloxycoumarin (400 mg, 1.16 mmoles) of Example 4 was dissolved in 4 ml dimethyl sulfoxide at room temperature with copper (II) bromide (260 mg, 1.16 mmoles) in 5 ml dimethyl sulfoxide added dropwise. Immediate effervesence was evidenced and stirring was continued overnight. The solvent was removed in vacuo and the product was recovered as a red oil. The oil was dissolved in chloroform, washed with two 1 ml portions of water, 1 ml saturated aqueous sodium bisulfite and dried over magnesium sulfate. The solvent was evaporated and the crude yield was 0.200 g (56% yield). The mixture was purified by silica gel chromatography with elution by 5% methanol/95% chloroform. Tan crystals had mp 134–135.5° C.; $^1$H-nmr (deuteriochloroform):δ 2.18 (s, 3H), 2.31 (s, 3H), 3.38 (t, J=6 Hz, 1H), 3.54 (t, 1H), 3.78–3.92 (m, 1H), 4.44–4.56 (m, 1H), 4.68 (t, J=9 Hz, 1H), 6.03 (s, 1H), 7.15 (s, 1H); $^{13}$C-nmr (deuteriochloroform):δ 8.8, 19.5, 35.1, 44.6, 77.4, 111.7, 114.3, 117.7, 124.3, 125.1, 153.1, 154.1, 161.7, 162.2 δ ms: (EI) m/z (relative intensity) 311 (M$^+$, 20), 310 (M$^+$, 70) 309 (23), 308 (70), 215 (base), 187 (48).

Anal. Calcd. for $C_{14}H_{13}BrO_3$: C, 54.39; H, 4.24. Found: C, 54.55; H, 4.29.

Example 8

3-Bromo-4,8-dimethyl-4'-bromomethyl-4', 5'-dihydropsoralen

The 4,8-dimethyl-4'-bromomethyl-4',5'-dihydropsoralen (450 mg, 1.45 mmoles) of Example 7 was dissolved in 20 ml chloroform before the addition of N-bromosuccinimide (0.258 g, 1.449 mmoles) at room temperature. The reaction mixture was stirred overnight and washed with two 1 ml portions of saturated aqueous sodium bisulfite followed by washing with two 1 ml portions of water and drying with magnesium sulfate. Elution of product by 5% methanol/95% chloroform on silica gel recovered 0.430 g (76% yield) tan crystals: mp 148–150° C.; $^1$H-nmr (deuteriochloroform):δ 2.17 (s, 3H), 2.48 (s, 3H), 3.50 (d, J=9 Hz, 1H), 3.58–3.70 (m, 1H), 3.89–4.05 (m, 1H), 4.53–4.64 (m, 1H), 4.79 (t, J=9 Hz, 1H), 7.38 (s, 1H); ms: (EI) m/z (relative intensity) 391 (M$^+$, 35), 390 (M$^+$, 40), 389 (M$^+$, base) 388 (38), 115 (10).

Anal. Calcd. for $C_{14}H_{12}Br_2O_3$: C, 43.33; H, 3.12. Found: C, 43.56; H, 3.26.

III. Synthesis of 4,8-dimethyl-4'-pyridiniummethyl-4',5'-dihydropsoralen Halide Salts

Example 9

4,8-Dimethyl-4'-pyridiniummethyl-4',5'-dihydropsoralen Iodide Salt

Two ml pyridine was added to 4,8-dimethyl-4'-iodomethyl-4',5'-dihydropsoralen (150 mg, 0.421 mmoles), of Example 5 and the mixture was heated at reflux for 2 hours. Solids formed upon cooling and pyridine was evaporated in vacuo. Residual pyridine was removed by placing the flask on a vacuum pump overnight. Solids were refluxed in chloroform for one hour to solubilize 4,8,4'-trimethylpsoralen which formed as the major product. Undissolved quaternary compound was recovered by Filtration and washed with 0.5 ml acetone then with 0.5 ml ether. The 4,8-dimethyl-4'-pyridiniummethyl-4',5'-dihydropsoralen iodide salt was recrystallized from ethanol slowly and 22 mg (12% yield) bright tan crystals were recovered: mp 290–292° C.; $^1$H-nmr (methanol-d4):δ 2.21 (s, 3H), 2.33 (s, 3H), 4.20–4.28 (m, 1H), 4.73 (d, 2H), 4.87–4.97 (m, 2H), 6.16 (s, 1H), 7.15 (s, 1H), 8.13 (t, J=6.1 Hz, 2H), 8.63 (t, J=8.5 Hz, 1H), 8.93 (d, J=6.1 Hz, 2H).

Anal. Calcd. for C19H18INO3: C, 52.43; H, 4.17; N, 3.22. Found: C, 52.26; H, 4.02, N, 3.21.

Example 10

4,8,4'-trimethylpsoralen

The major product, 4,8,4'-trimethylpsoralen, was recovered from the chloroform layer by removal of solvent in vacuo and recrystallization from ethanol. $^1$H-nmr (deuteriochloroform):δ 2.19 (s, 3H), 2.43 (s, 3H), 2.46 (s, 3H), 6.16 (s, 1H), 7.44 (s, 1H), 7.51 (s, 1H).

Example 11

4,8-Dimethyl-4'-(N-4"-methyl-pyridiniummethyl)-4',5'-dihydropsoralen Iodide Salt 4,8-Dimethyl-4'-iodomethyl-4',5'-dihydropsoralen (138 mg, 0.389 mmoles) of Example 5 was dissolved in 2 ml of 4"-methyl-pyridine and the mixture was reacted for 2 hours at 105 C. The mixture was then allowed to cool down to room temperature and the pyridine was removed by evaporation under reduced pressure. The crude product was recrystallized from chloroform to yield the pyridinium salt as a yellow solid (31 mg, 18% yield): $^1$H-nmr (methanol-d4):δ 2.20 (s, 3H), 2.35 (d, J=0.9 Hz, 3H), 2.70 (s, 3H), 4.20–4.28 (m, 1H), 4.68–4.73 (m, 2H), 4.82–4.92 (m, 2H), 6.16 (d, J=0.8 Hz, 1H), 7.22 (s, 1H), 7.95 (d, J=6.3 Hz, 2H), 8.75 (d, J=6.5 Hz, 2H).

Anal. Calcd for C20H20NIO3 0.25 moles H2O: C, 52.99; H, 4.56; N, 3.09. Found: C, 52.88; H, 4.50; N, 3.04.

From the remaining organic layer, was purified (69.5 mg, 78%) of 4,8,4'-trimethylpsoralen 10 by performing a flash silica gel column chromatography (chloroform).

Example 12

3-Bromo-4,8-dimethyl-4'-pyridiniummethyl-4',5'-dihydropsoralen Iodide Salt

One ml pyridine was added to 3-bromo-4,8-dimethyl-4'-iodomethyl-4',5'-dihydropsoralen (130 mg, 0.308 mmoles) of Example 6 and the mixture was heated at reflux for 2 hours. Solids formed upon cooling, and pyridine was evaporated in vacuo. Residual pyridine was removed by placing the flask on a vacuum pump overnight. Solids were refluxed in chloroform for one hour to solubilize 3-bromo-4,8,4'-trimethylpsoralen which formed as the major product (0.065 g recovered). Undissolved quaternary compound was recovered by filtration and washed with acetone to remove the slight red coloration and was rinsed again with ether. The 4,8-dimethyl-4'-pyridiniummethyl-4',5'-dihydropsoralen iodide salt was recrystallized from ethanol slowly, and 18 mg (11% yield) of tan crystals: mp above 270° C.; $^1$H-nmr (methanol-d$_4$):δ 2.28 (s, 3H), 2.52 (s, 3H), 4.22–4.30 (m, 1H), 4.73 (d, 2H), 4.87–4.97 (m, 2H), 7.22 (s, 1H), 8.13 (t, 2H), 8.66 (t, 1H), 8.91 (d, 2H).

Anal. Calcd. for $C_{19}H_{17}BrINO_3$: C, 44.39; H, 3.33, N, 2.72. Found: C, 44.39; H, 3.24, N, 2.68.

Example 13

4.8-Dimethyl-4'-pyridiniummethyl-4',5'-dihydropsoralen Bromide Salt

The 4,8-dimethyl-4'-bromomethyl-4',5'-dihydropsoralen (180 mg, 0.580 mmoles) of Example 7 was added to 2 ml pyridine and heated at 110° C. for two hours with stirring. The residual pyridine was removed in vacuo and remaining solids were refluxed in 20 ml chloroform. Undissolved solids were collected by filtration and recrystallized from ethanol. The recovered yield was 99 mg (43% yield) tan crystals: mp 283.2–283.8° C.; $^1$H-nmr (dimethylsulfoxide-d$_6$):δ 2.13 (s, 3H), 2.45 (s, 3H), 4.16–4.36 (m, 1H), 4.64–4.70 (m, 2H), 4.86–4.92 (m, 2H), 6.06 (s, 1H), 7.28 (s, 1H), 8.15 (t, J=7 Hz, 2H), 8.61 (dd, J$_1$=8 Hz, J$_2$=8 Hz 1H), 8.95 (d, J=6.2 Hz, 2H).

Anal. Calcd. for $C_{19}H_{18}BrNO_3$.0.36 moles $H_2O$: C, 57.81; H, 4.77; N, 3.55. Found: C, 57.81; H, 4.61; N, 3.46.

The chloroform layer was dried to yield 4,8,4'-trimethylpsoralen 10 as the major product.

Example 14

3-Bromo-4,8-dimethyl-4'-pyridiniummethyl-4',5'-dihydropsoralen Bromide Salt

3-Bromo-4,8-dimethyl-4'-bromomethyl (125 mg, 0.332 mmoles) of Example 8 was added to 2 ml pyridine and heated at 110° C. for two hours with stirring. The residual pyridine was removed in vacuo and remaining solids were refluxed in 20 ml chloroform. Undissolved solids were collected by filtration and recrystallized from ethanol. The recovered yield was 0.079 g (52% yield): decomposition occurred above 280° C.; $^1$H-nmr (methanol-d4):δ 2.21 (s, 3H), 2.33 (s, 3H), 4.20–4.28 (m, 1H), 4.73 (d, 2H), 4.87–4.97 (ni, 211), 7.15 (s, 1H), 8.13 (t, J=6.1 Hz, 2H), 8.63 (t, J=8.5 Hz, 1H), 8.93 (d, J=6.1 Hz, 2H).

Anal. Calcd. for $C_{19}H_{17}Br_2NO_3$ 0.2 moles $H_2O$: C, 48.46; H, 3.72; N, 2.98. Found: C, 48.46; H, 3.67; N, 2.94.

The chloroform layer was dried to yield 3-bromo-4,8,4'-trimethylpsoralen as the other major product.

IV: Synthesis of 4,8-dimethyl-4'-cyanomethyl-4',5'-dihydropsoralen

Example 15

4,8-Dimethyl-4'-cyanomethyl-4',5'-dihydropsoralen

A solution of 6-diazoniumtetrafluoroborate-4,8-dimethyl-7-allyloxycoumarin (100 mg, 0.298 mmoles) of Example 4 in 1.4 ml dimethylsulfoxide was added to copper (I) cyanide (26 mg, 029 mmoles) in 1.4 ml pyridine which had been stirred for ten minutes. An immediate evolution of gas was accompanied by the darkening of the solution. After twenty minutes the solvents were removed in vacuo. The organic portion was dissolved in 4 ml chloroform and washed with two 1 ml portions of water. The chloroform was removed in vacuo and the resulting orange solid was purified by silica gel column chromatography, with elution by 5% methanol/95% chloroform. The crystals weighed 32 mg (42% yield): mp 156–157° C.; $^1$H-nmr (deuteriochloroform):δ 2.23 (s, 3H), 2.42 (s, 3H), 2.73 (t, J=6 Hz, 2H), 3.78–3.97 (m, 1H), 4.40–4.54 (m, 1H), 4.74–4.88 (m, 1H), 6.16 (s, 1H), 7.44 (s, 1H); ms: (EI) m/z (relative intensity) 257 (M$^+$, 16), 256 (M$^+$, Base) 255 (19), 215 (26), 181 (48), 181 (17).

Anal. Calcd. for $C_{15}H_{13}NO_3$ 0.33 moles H2O: C, 68.99; H, 5.26. Found: C, 68.99; H, 5.29.

V. Pharmacological Assay

Representative examples of the compounds described and claimed herein were tested in this assay for biological activity and found to be potent inhibitors of cell growth. Inhibition of cell growth was rapid, dependent on concentration, and required light activation. These findings directly demonstrate that the newly synthesized compounds are potential phototherapeutics for human proliferative diseases. A description of this assay follows.

Example 16

The photobiological activity was assayed using a keratinocyte cell line grown in a monolayer culture. In this assay, PAM 212 keratinocytes were grown in Dulbecco's Modified Eagle's medium supplemented with 10% newborn calf serum in a 5% carbon dioxide incubator. Cells were inoculated into 6-well Falcon plastic culture dishes at 25,000 cells per well. After 24 hours, the medium was charged to fresh growth medium supplemented with increasing concentrations of the test compounds or the control medium. Controls and test concentrations were analyzed in triplicate.

These plates were then incubated in a 37° C. carbon dioxide incubator. After 30 minutes culture plates were exposed to UVA light (UVA, 320–400 nm) emitted from a bank of four BLB fluorescent light tubes (F40 BL, Sylvania) placed approximately 10 cm above the cell culture plates. The incident light on the culture plates was 2.4 mW/cm$^2$ as measured with an International Light UV radiometer, Model IL 442A. The cells were exposed to 1.28J/square centimeter of UVA.

After completion of the irradiation phase, the cell culture medium was drained, the cells refed with fresh growth medium and then re-incubated in the carbon dioxide incubator to allow for cell growth. After 4–5 days of growth the culture plates were removed from the incubator and the cell culture medium was drained. The cells were detached from the plates with trypsin and counted in a Coulter Counter. For control cells or for cells treated with test compounds, cell growth was determined as a percentage of control. The concentration at which a given photoactivated test compound inhibited growth by 50% (the IC$_{50}$ in micromolar concentration, $\mu$M) was determined from die growth inhibition data. This value is shown in Table I for a variety of phototherapeutics.

TABLE I

| | Toxicity (IC$_{50}$ values in $\mu$M) | |
|---|---|---|
| Example | Photo-toxicity | Dark-toxicity |
| 1 | >300 | |
| 2 | 5 | >100 |
| 3 | 240 | >100 |
| 5 | 0.1 | >100 |
| 6 | 0.2–0.5 | |
| 9 | 0.5 | |
| 12 | >30 | 70 |
| 15 | 3 | >100 |

The claimed invention is:

1. A 4'-substituted-4,8-dimethyl-4',5'-dihydropsoralen of formula (V):

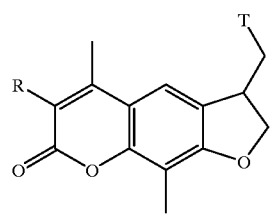

wherein
  R is hydrogen, a halogen, CN, or an acyl group;
  T is a halogen, CN a carboxylate, a carboalkoxy group or a group defined by NR$^1$R$^1$ or (N$^+$R$^1$ R$^2$R$^3$)X$^-$,
  R$^1$ and R$^2$ are independently a C$_1$–C$_6$ alkyl, or R$^1$ and R$^2$ together with the nitrogen form a 5–8 member heterocyclic ring, or when T is a group defined by (N$^+$R$^1$R$^2$R$^3$)X$^-$, R$^1$ and R$^2$ together with the nitrogen form a 5–8 member heterocyclic ring or heterocyclic aromatic ring,
  R$^3$ is hydrogen, a C$_1$–C$_{12}$ alkyl, or, when R$^1$ and R$^2$ together with the nitrogen form a heterocyclic aromatic ring, R$^3$ is a double bond within the heterocyclic aromatic ring;
  X is a halide;

or a pharmaceutically acceptable salt thereof.

2. A 4'-substituted 4,8-dimethyl-4',5'-dihydropsoralen of claim 1, wherein

R is hydrogen, F, Br, I, CN, propionyl, acetyl, or phenylacetyl;

T is Br, I, CN, a carboalkoxy group, or a group defined by $NR^1R^2$ or $(N^+ R^1R^2R^3)X^-$, $R^1$ and $R^2$ are independently methyl, ethyl, hydroxyethyl, or propyl, or $R^1$ and $R^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-($C_1$–$C_4$ alkyl)pyridinyl, N-hexamethyleneiminyl, or N-heptamethyleneiminyl;

$R^3$ is hydrogen, methyl, ethyl, dodecyl, or when $R^1$ and $R^2$ together with the nitrogen form a heterocyclic aromatic ring, $R^3$ is a double bond within the heterocyclic aromatic ring; $X^-$ is a bromide or iodide.

3. A 4-substituted 4,8-dimethyl-4',5'-dihydropsoralen of claim 2, wherein $R^1$ and $R^2$ together with the nitrogen form a heterocyclic ring selected from N-morpholinyl, N-pyridinyl, N-4-ethylpyridinyl, 4-methylpyridinyl, or N-quinolinyl.

4. A 4'-substituted 4,8-dimethyl-4',5'-dihydropsoralen of claim 1, wherein

R is hydrogen, F, Br, I, CN, propionyl, acetyl, or phenylacetyl and

T is Br, I, CN, a carboxylate, or a carboalkoxy group.

5. A 4'-substituted 4,8-dimethyl-4',5'-dihydropsoralen of claim 1, wherein T is a group defined by $NR^1R^2$ or $(N^+R^1R^2R^3)X^-$; when T is a group defined by $NR^1R^2$, R' and $R^2$ together with the nitrogen form a 5–8 member heterocyclic ring, or when T is a group defined by $(N^+R^1R^2R^3)X^-$, $R^1$ and $R^2$ together with the nitrogen form a 5–8 member heterocyclic ring or heterocyclic aromatic ring.

6. A 4'-substituted 4,8-dimethyl-4',5'-dihydropsoralen of claim 1, selected from 4,8-Dimethyl-4'-(bromomethyl)-4',5'-dihydropsoralen;

4,8-Dimethyl-4'-(iodomethyl)-4',5'-dihydropsoralen;

4,8-Dimethyl-4'-(N-pyridiniummethyl)-4',5'-dihydropsoralen bromide salt;

4,8-Dimethyl-4'-(N-4-ethylpyridiniummethyl)-4',5'-dihydropsoralen bromide salt;

4,8-Dimethyl-4'-(N-4-methylpyridiniummethyl)-4',5'-dihydropsoralen bromide salt;

4,8-Dimethyl-4'-(N-quinoliniummethyl)-4',5'-dihydropsoralen bromide salt;

4,8-Dimethyl-4'-(N,N,N-trimethylammonium methyl)-4',5'-dihydropsoralen bromide salt;

3-Bromo-4,8-Dimethyl-4'-(bromomethyl)-4',5'-dihydropsoralen;

3-Bromo-4,8-Dimethyl-4'-(iodomethyl)-4',5'-dihydropsoralen;

3-Bromo-4,8-dimethyl-4'-(N-pyridiniummethyl)-4',5'-dihydropsoralen bromide salt;

3-Bromo-4,8-dimethyl-4'-(N-4-ethylpyridiniummethyl)-4',5-dihydropsoralen bromide salt;

3-Bromo-4,8-dimethyl-4'-(N-4-methylpyridiniummethyl)-4',5-dihydropsoralen bromide salt;

3-Bromo-4,8-dimethyl-4'-(N-pyridiniummethyl)-4',5'-dihydropsoralen iodide salt;

3-Bromo-4,8-dimethyl-4'-(N-quinoliniummethyl)-4',5'-dihydropsoralen bromide salt;

3-Bromo-4,8-dimethyl-4'-(N,N,N-trimethylammoniummethyl)-4',5'-dihydropsoralen bromide salt;

3-Bromo-4,8-dimethyl-4'-(N,N,N-trimethylammoniummethyl)-4',5'-dihydropsoralen iodide salt;

3-Iodo-4,8-dimethyl-4'-(iodomethyl)-4',5'-dihydropsoralen;

3-Cyano-4,8-dimethyl-4'-(bromomethyl)-4',5'-dihydropsoralen;

3-Cyano-4,8-dimethyl-4'-(iodomethyl)-4',5'-dihydropsoralen;

3-Cyano-4,8-dimethyl-4'-(N-pyridiniummethyl)-4',5'-dihydropsoralen bromide salt;

3-Cyano-4,8-dimethyl-4'-(N-pyridiniummethyl)-4',5'-dihydropsoralen iodide salt;

3-Cyano-4,8-dimethyl-4'-(N-4-ethylpyridiniummethyl)-4',5'-dihydropsoralen bromide salt;

3-Cyano-4,8-dimethyl-4'-(N-4-methylpyridiniummethyl)-4',5'-dihydropsoralen bromide salt;

3-Cyano-4,8-dimethyl-4'-(N,N,N-trimethylammoniummethyl)-4',5'-dihydropsoralen bromide salt;

3-Cyano-4,8-dimethyl-4'-(N,N,N-trimethylammoniummethyl)-4',5'-dihydropsoralen iodide salt;

3-Fluoro-4,8-dimethyl-4'-(bromomethyl)-4',5'-dihydropsoralen;

3-Fluoro-4,8-dimethyl-4'-(iodomethyl)-4',5'-dihydropsoralen;

3-Fluoro-4,8-dimethyl-4'-(N-pyridiniummethyl)-4',5'-dihydropsoralen bromide salt;

3-Fluoro-4,8-dimethyl-4'-(N-ethylpyridiniummethyl)-4',5'-dihydropsoralen bromide salt;

3-Fluoro-4,8-dimethyl-4'-(N-4-methylpyridiniummethyl)-4',5'-dihydropsoralen bromide salt;

3-Fluoro-4,8-dimethyl-4'-(N-quinoliniummethyl)-4',5'-dihydropsoralen bromide salt;

3-Fluoro-4,8-dimethyl-4'-(N,N,N-trimethylammonium methyl)-4',5'-dihydropsoralen bromide salt;

3-Fluoro-4,8-dimethyl-4'-(iodomethyl)-4',5'-dihydropsoralen;

4,8-Dimethyl-4'-(N,N-diethanolaminomethyl)-4',5'-dihydropsoralen;

4,8-Dimethyl-4'-(N,N-dimethylaminomethyl)-4',5'-dihydropsoralen hydroiodide salt;

4,8-Dimethyl-4'-(N-morpholinomethyl)-4',5'-dihydropsoralen;

4,8-Dimethyl-4'-(N-2,6-dimethylmorpholinomethyl)-4',5'-dihydropsoralen; or a pharmaceutically acceptable salt thereof.

7. A process for preparing a 4'-substituted 4,8-dimethyl-4',5'-dihydropsoralen of formula (V):

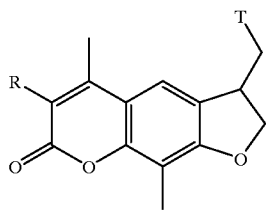

wherein
R is hydrogen, a halogen, CN or an acyl group;
T is a halogen, a carboxylate, a carboalkoxy group or CN, the process comprising the step of reacting a 4,8-dimethyl-6-diazoniumtetra-fluoroborate-7-allyloxycoumarin of the formula (IV):

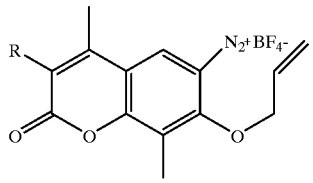

IV with a cyclization reagent under conditions to form said 4'-substituted 4,8-dimethyl-4',5'-dihydropsoralen;
when T is Br, the cyclization reagent is $CuBr_2$;
when T is 1, the cyclization reagent is $NaI/I_2$; and
when T is CN, the cyclization reagent is CuCN.

8. A process for preparing a 4'-substituted 4,8-dimethyl-4',5'-dihydropsoralen of claim 7, wherein
R is hydrogen, F, Br, I, CN, propionyl, acetyl, or phenylacetyl; and T is Br, I, or CN.

9. A process for preparing 4'-N-aminomethyl substituted 4,8-dimethyl-4',5'-dihydropsoralen of the formula (V):

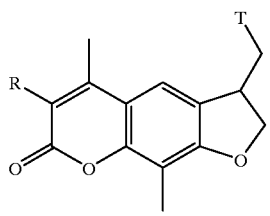

V wherein
R is hydrogen, a halogen, CN, or an acyl group;
T is $NR^1R^2$ or $(N^+R^1R^2R^3)X^-$;
$R^1$ and $R^2$ are independently a $C_1$–$C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or a 6-member heterocyclic aromatic ring;
$R^3$ is hydrogen, a $C_1$–$C_{12}$ alkyl, or, when $R^1$ and $R^2$ together with the nitrogen form a heterocyclic aromatic ring, $R^3$ is a double bond within the heterocyclic aromatic ring;
$X^-$ is bromide or iodide;
comprising the steps of:

reacting a 4,8-dimethyl-4'-halomethyl-4',5'-dihydropsoralen of the formula:

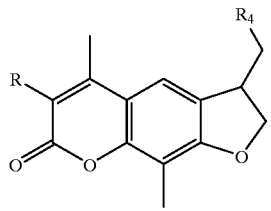

wherein
$R_4$ is a halogen and R is as defined above, with a secondary or tertiary amine to form a 4'-N-aminomethyl substituted 4,8-dimethyl-4',5'-dihydropsoralen of the formula (V):

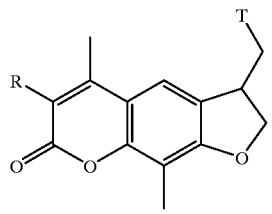

V wherein
R and T are as defined above.

10. A process according to claim 9, wherein the amine is pyridine, methylpyridine, ethylpyridine, morpholine, diethanolamine and dimethylamine.

11. A process for preparing 4'-N-aminomethyl substituted 4,8-dimethyl-4',5'-dihydropsoralen of claim 10, wherein
R is hydrogen, F, Br, I, CN, or an acyl group;
$R^1$ and $R^2$ are independently methyl, ethyl, hydroxyethyl, or propyl, or $R^1$ and $R^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-($C_1$–$C_4$ alkyl)pyridinyl, N-hexamethyleneiminyl, N-heptamethyleneiminyl, N-quinolinyl or N-isoquinolyl; and
$R^3$ is hydrogen, methyl, ethyl, dodecyl, or a double bond within a heterocyclic aromatic ring defined by N, $R^1$, and $R^2$.

12. A process for preparing 4'-N-aminomethyl substituted 4,8-dimethyl-4',5'-dihydropsoralen of claim 10, wherein
R is hydrogen, F, Br, I, CN, or an acyl group; and
$R^1$ and $R^2$ are independently methyl, 2-hydroxyethyl, or propyl, or $R^1$ and $R^2$ together with the nitrogen form a heterocyclic ring selected from N-morpholinyl, N-pyridinyl, N-4-ethylpyridinyl, 4-methylpyridinyl or N-quinolinyl; and
$R^3$ is hydrogen, methyl, dodecyl, or a double bond within a heterocyclic aromatic ring defined by N, $R^1$, and $R^2$.

13. A method for treating a proliferative disorder in a mammal comprising administering to the mammal an effective amount of a compound according to claim 1 and then irradiating the mammal with ultraviolet light.

14. A method according to claim 13, wherein the compound is administered, topically, parenterally, or orally.

15. A pharmaceutical composition to treat a proliferative disorder comprising a therapeutically effective amount of a compound according to claim 1 and a pharmaceutically acceptable carrier.

16. A method for treating a disease of the blood or bone marrow of a mammal comprising the steps of:
   obtaining cells from the blood or marrow of the mammal,
   introducing into the cells an effective amount of a compound according to claim 1,
   exposing the cells containing the compound to ultraviolet radiation.

17. A method for treating a disease of the blood or bone marrow in a mammal comprising the steps of:
   obtaining cells from the blood or marrow of the mammal,
   introducing in vitro into the cells an effective amount of a compound according to claim 1,
   exposing the cells containing the compound to ultraviolet radiation, and
   returning the cells to the blood or bone marrow of the mammal.

18. A method for treating a disease of the blood or bone marrow in a mammal comprising the steps of:
   administering to the mammal an effective amount of a compound according to claim 1,
   obtaining cells from the blood or marrow of the mammal,
   exposing the cells to ultraviolet radiation, and
   returning the cells to the blood or bone marrow of the mammal.

19. A pharmaceutical composition to treat a disease of the blood or bone marrow of a mammal comprising a therapeutically effective amount of a compound according to claim 1 and a pharmaceutically acceptable carrier.

20. A pharmaceutical composition to treat a microbial infection in a mammal comprising a therapeutically effective amount of a compound according to claim 1 and a pharmaceutically acceptable carrier.

21. A method for treating a microbial infection comprising the step of administering to a mammal, in need of such treatment, a therapeutically effective amount of a photochemotherapeutic composition according to claim 1 and irradiating said patient with sufficient UVA to activate the therapeutic activity of said compound.

22. A microbicide composition comprising a compound of claim 1 in an amount effective to control the growth of at least one microorganism.

23. A method for controlling the growth of a microorganism on a substrate comprising the step of contacting a substrate susceptible to the growth of microorganisms with an effective amount of a compound of claim 1 to control the growth of at least one microorganism on the substrate.

24. A method for controlling the growth of microorganisms in an aqueous system capable of supporting growth of a microorganism comprising the step of treating the aqueous system with an amount of a compound of claim 1 effective to control the growth of at least one microorganism in the aqueous system.

* * * * *

UNITED STATES PATENT AND TRADEMARK OFFICE
CERTIFICATE OF CORRECTION

PATENT NO. : 6,177,424 B1  
DATED : January 23, 2001  
INVENTOR(S) : Ned D. Heindel et al.

Page 1 of 1

It is certified that error appears in the above-identified patent and that said Letters Patent is hereby corrected as shown below:

Column 22,  
Line 55, change "CN" to -- CN, --;  
Line 56, change "$NR^1R^1$" to -- $NR^1R^2$ --.

Column 23,  
Line 34, change "$R^1$" to -- $R^1$ --.

Coumn 25,  
Line 33, change "T is 1" to -- T is I --;  
Line 38, change "Tris" to -- T is --.

Signed and Sealed this

Sixteenth Day of October, 2001

Attest:

NICHOLAS P. GODICI  
*Attesting Officer*     *Acting Director of the United States Patent and Trademark Office*